(12) United States Patent
Horibe et al.

(10) Patent No.: US 11,320,419 B2
(45) Date of Patent: May 3, 2022

(54) SAMPLING OF BREATH GAS (71) Applicant: INTERNATIONAL BUSINESS MACHINES CORPORATION, Armonk, NY (US)

(72) Inventors: Akihiro Horibe, Yokohama (JP); Kuniaki Sueoka, Sagamihara (JP); Toru Aihara, Yokohama (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 351 days.

(21) Appl. No.: 16/777,424

(22) Filed: Jan. 30, 2020

(65) Prior Publication Data

US 2021/0239679 A1 Aug. 5, 2021

(51) Int. Cl.
*G01N 33/497* (2006.01)
*A61B 5/097* (2006.01)
*H01J 49/04* (2006.01)
*H01J 49/26* (2006.01)
*A61B 5/08* (2006.01)

(52) U.S. Cl.
CPC ........... *G01N 33/497* (2013.01); *A61B 5/082* (2013.01); *A61B 5/097* (2013.01); *H01J 49/0422* (2013.01); *H01J 49/26* (2013.01)

(58) Field of Classification Search
CPC ............. G01N 33/497; G01N 33/4972; G01N 2033/4975; G01N 2033/4977; G01N 2001/2244; A61B 5/082; A61B 5/083; A61B 5/0833; A61B 5/0836; A61B 5/097; A61M 2230/43; A61M 2230/432; A61M 2230/435; A61M 2230/437; Y10S 436/90
See application file for complete search history.

(56) References Cited

U.S. PATENT DOCUMENTS

2009/0318823 A1 * 12/2009 Christman ............. A61B 5/097
600/532
2014/0276100 A1 9/2014 Satterfield et al.

FOREIGN PATENT DOCUMENTS

| CN | 201870661 U | | 6/2011 | |
|---|---|---|---|---|
| CN | 203619536 U | * | 6/2014 | |
| CN | 203619536 U | | 6/2014 | |
| CN | 206656892 U | * | 11/2017 | |
| CN | 206656892 U | | 11/2017 | |
| WO | WO-2008060165 A1 | * | 5/2008 | ............ A61B 5/097 |
| WO | WO-2013040494 A1 | * | 3/2013 | ............ A61B 5/082 |
| WO | WO-2013090705 A1 | * | 6/2013 | ........... A61B 5/0002 |
| WO | WO-2013095284 A1 | * | 6/2013 | ............ A61B 5/082 |
| WO | WO-2015134390 A1 | * | 9/2015 | ............ A61B 5/082 |
| WO | WO-2016140389 A1 | * | 9/2016 | ............... A61B 5/02 |
| WO | WO-2021021299 A1 | * | 2/2021 | |

* cited by examiner

*Primary Examiner* — Herbert K Roberts
(74) *Attorney, Agent, or Firm* — Tutunjian & Bitetto, P.C.; Randall Bluestone (57) ABSTRACT

A method for sampling breath gas, includes collecting a first breath sample in a first bag. The first breath sample is an initial part of expired gas expired after inspiration. Additionally, the method includes collecting a second breath sample in a second bag. The second breath sample is a latter part of the expired gas. The method includes subtracting first mass spectral data obtained by mass spectroscopy of the first breath sample collected in the first bag from second mass spectral data obtained by mass spectroscopy of the second breath sample collected in the second bag.

20 Claims, 6 Drawing Sheets

SAMPLING OF BREATH GAS

BACKGROUND

The present invention relates to sampling breath gas.

A breath sample is collected for breath gas analysis by mass spectroscopy for the purpose of, for example, rapid and non-invasive blood vapor detection.

SUMMARY

According to an embodiment of the present invention, there is provided a method for sampling breath gas. The method includes collecting a first breath sample in a first bag. The first breath sample is an initial part of expired gas expired after inspiration. The method further includes collecting a second breath sample in a second bag. The second breath sample is a latter part of the expired gas. The method further includes subtracting first mass spectral data from second mass spectral data. The first mass spectral data is obtained by mass spectroscopy of the first breath sample collected in the first bag. The second mass spectral data is obtained by mass spectroscopy of the second breath sample collected in the second bag.

According to another embodiment of the present invention, there is provided an apparatus for sampling breath gas. The apparatus includes a first bag, a second bag, and a controller. The controller is for controlling a first breath sample to flow in the first bag and controlling a second breath sample to flow in the second bag so that first mass spectral data is subtracted from second mass spectral data. The first breath sample is an initial part of expired gas expired after inspiration. The second breath sample is a latter part of the expired gas. The first mass spectral data is obtained by mass spectroscopy of the first breath sample in the first bag. The second mass spectral data is obtained by mass spectroscopy of the second breath sample in the second bag.

According to yet another embodiment of the present invention, there is provided a system for analyzing breath gas. The system includes a bag unit which includes a first bag and a second bag. The first bag is a bag in which a first breath sample is collected. The first breath sample is an initial part of expired gas expired after inspiration. The second bag is a bag in which a second breath sample is collected. The second breath sample is a latter part of the expired gas. The system further includes a mass spectrometer which obtains first mass spectral data and second mass spectral data. The first mass spectral data is obtained by mass spectroscopy of the first breath sample collected in the first bag, and the second mass spectral data is obtained by mass spectroscopy of the second breath sample collected in the second bag. The system further includes a data processor which subtracts the first mass spectral data from the second mass spectral data.

DETAILED DESCRIPTION

Hereinafter, exemplary embodiments of the present invention will be described in detail with reference to the attached drawings.

It is to be noted that the present invention is not limited to the exemplary embodiments to be given below and can be implemented with various modifications within the scope of the present invention. In addition, the drawings used herein are for purposes of illustration, and may not show actual dimensions.

The breath sample is greatly affected by inspired environmental air. That is, the breath sample is the sum of breath gas and the inspired environmental air. Therefore, it is necessary to remove the inspired environmental air for high accuracy analysis. To remove the inspired environmental air, surrounding environmental air can be used as a reference sample, which is to be subtracted from the breath sample.

However, since the surrounding environmental air is not constant due to various influences of surroundings, it is not always the same as the inspired environmental air. Thus, the inspired environmental air cannot be completely removed by using surrounding environmental air as a reference sample.

In view of this, in the exemplary embodiment, the inspired environmental air can be used as the reference sample.

Specifically, breath gas expired immediately after inspiration can be used as the first breath sample (the reference sample). The first breath sample can be inspired environmental air which has come out of anatomical dead space without reaching lungs. The anatomical dead space is a space from a nasal cavity to a terminal bronchiole of an airway, which is not directly involved in gas exchange because there is no alveolus anatomically.

On the other hand, breath gas expired at a predetermined interval after expiration of the first breath sample is used as the second breath sample (breath sample from which the reference sample is to be subtracted). The second breath sample can be the sum of concentrated breath gas and inspired environmental air. This concentrated breath gas can be gas which has come out of lungs after being involved in gas exchange in alveoli, and this inspired environmental air can be gas which has come out of lungs without being involved in gas exchange in alveoli.

Thus, subtracting the first breath sample from the second breath sample results in the alveolar gas, which is pure breath gas.

Note that, strictly speaking, the first breath sample can include dilute breath gas which has come out of lungs after being slightly involved in gas exchange in alveoli. However, the dilute breath gas is negligibly dilute, so subtracting the first breath sample from the second breath sample results in substantially pure breath gas.

Figure 1:
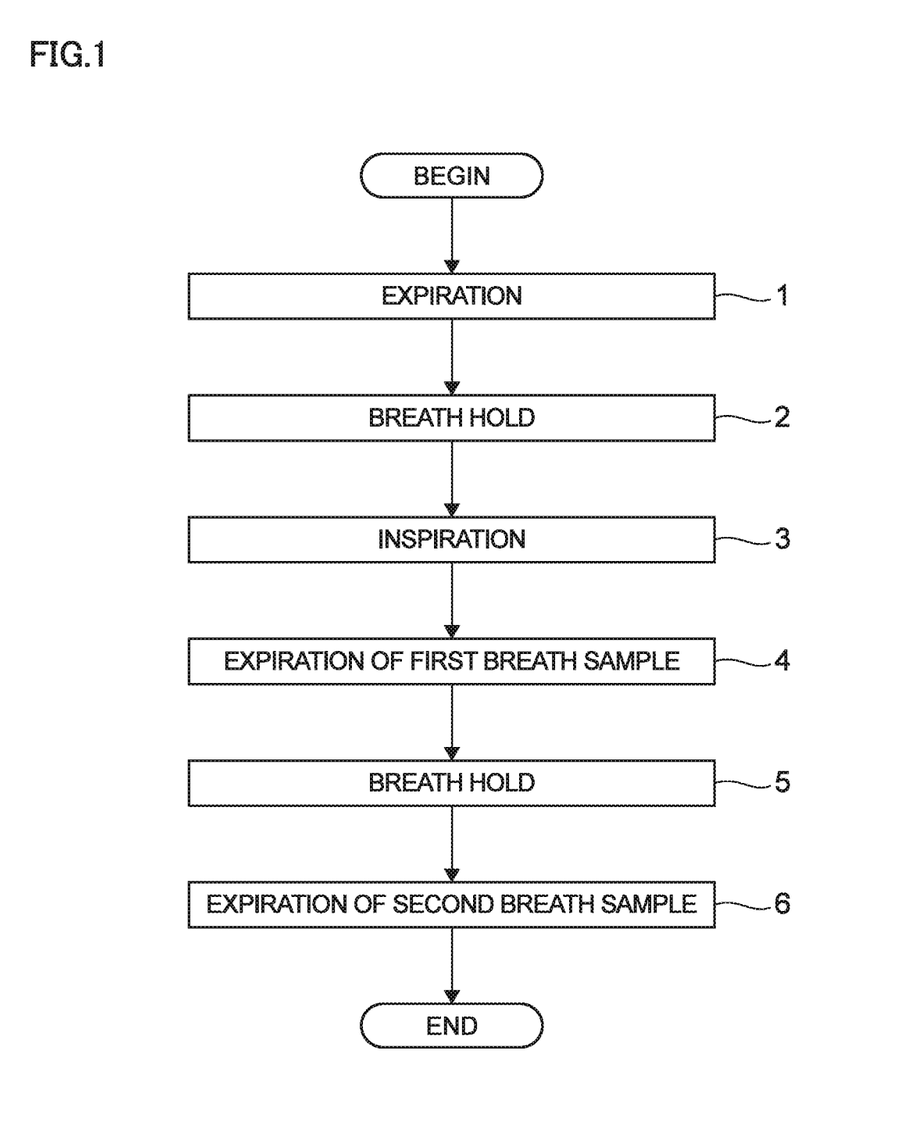
FIG. 1 depicts a flowchart representing an example of an operation of a subject who expires breath gas to be sampled according to an exemplary embodiment.

Referring to FIG. 1, there is shown a flowchart representing an example of an operation of a subject who expires breath gas to be sampled according to the exemplary embodiment.

First, the subject can expire, for example, 1000 milliliters of breath gas (block 1).

Then, the subject can perform breath hold for 5 seconds, for example (block 2). This breath hold can be performed to avoid re-taking in the breath gas expired at block 1.

And then, the subject can inspire, for example, 2000 to 3000 milliliters of breath gas (block 3).

After that, the subject can expire the first breath sample (block 4). The first breath sample can be an initial part of expired gas expired after inspiration at block 3. The first breath sample can be a predetermined volume of the expired gas expired immediately after inspiration at block 3. The predetermined volume can be, for example, 150 to 500 milliliters, because about 150 milliliters of inspired gas comes out of anatomical dead space without reaching lungs. As a result of block 4, the first breath sample can be collected.

Then, the subject can perform breath hold for a predetermined period of time (block 5). The predetermined period of time can be, for example, 10 to 30 seconds.

And then, the subject can expire the second breath sample (block 6). The second breath sample can be a latter part of the expired gas expired after inspiration at block 3. The second breath sample can be a predetermined volume of the expired gas expired at a predetermined interval (namely, after the predetermined period of time passed at block 5), after expiration of the first breath sample at block 4. The predetermined volume can be, for example, 1000 milliliters. As a result of block 6, the second breath sample can be collected.

Figure 2:
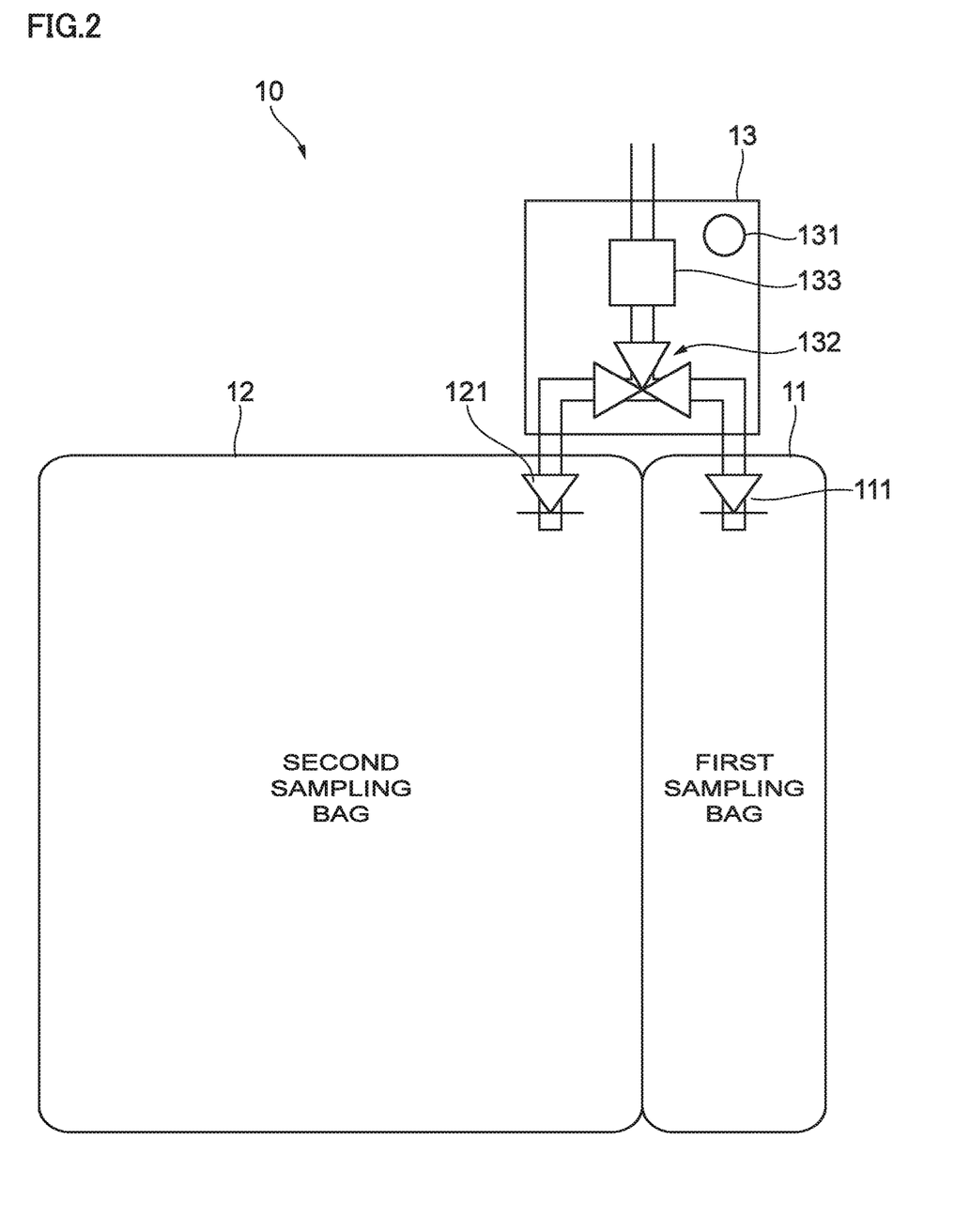
FIG. 2 depicts an example of a configuration of a sampling bag module according to the exemplary embodiment.

Referring to FIG. 2, there is shown an example of a configuration of a sampling bag module 10 according to the exemplary embodiment. As shown in FIG. 2, the sampling bag module 10 can include a first sampling bag 11, a second sampling bag 12, and a sampling control device 13.

The first sampling bag 11 can be provided to store the first breath sample. The first sampling bag 11 can have a predetermined volume according to the volume of the first breath sample. The predetermined volume can be, for example, 200 milliliters. In addition, the first sampling bag 11 can include a backflow prevention valve 111 for preventing the first breath sample from flowing backward to the sampling control device 13 side. The first sampling bag 11 serves as one example of the claimed first bag.

The second sampling bag 12 can be provided to store the second breath sample. The second sampling bag 12 can have a predetermined volume according to the volume of the second breath sample. The predetermined volume can be, for example, 1000 milliliters. In addition, the second sampling bag 12 can include a backflow prevention valve 121 for preventing the second breath sample from flowing backward to the sampling control device 13 side. The second sampling bag 12 serves as one example of the claimed second bag.

Note that both of the first sampling bag 11 and the second sampling bag 12 can be made of a material appropriately selected according to application of storing breath samples. The material can preferably have a low gas permeation property. Further, the material can preferably have a low elution property. For example, polyethylene terephthalate (PET) can be used as the material having a low elution property.

The sampling control device 13 can control the first breath sample to flow in the first sampling bag 11 and control the second breath sample to flow in the second sampling bag 12. The sampling control device 13 serves as one example of the claimed controller. The sampling control device 13 can include a switch 131, a three-way valve 132, and a gas flow meter 133.

The switch 131 can be pushed to activate the sampling control device 13. The switch 131 can also be pushed to start a guidance. The guidance can be voice guidance for the sampling process.

The three-way valve 132 can be manipulated to control gas flow into either of the first sampling bag 11 and the second sampling bag 12 at each timing. Alternatively, the three-way valve 132 can be automatically operated to control the gas flow.

The gas flow meter 133 can record information such as gas flow speed, gas flow volume, and gas flow time. Note that this recorded information can be used as additional information when mass spectral data of the breath sample is analyzed.

In addition, the sampling control device 13 can include a secondary battery (not shown).

Note that the sampling control device 13 can be reusable, while the first sampling bag 11 and the second sampling bag 12 can be disposable.

Next, a breath gas measurement system according to the exemplary embodiment is described.

The breath gas measurement system can have two configurations. Hereinafter, one of them is described as the first exemplary embodiment and the other is described as the second exemplary embodiment.

Figure 3:
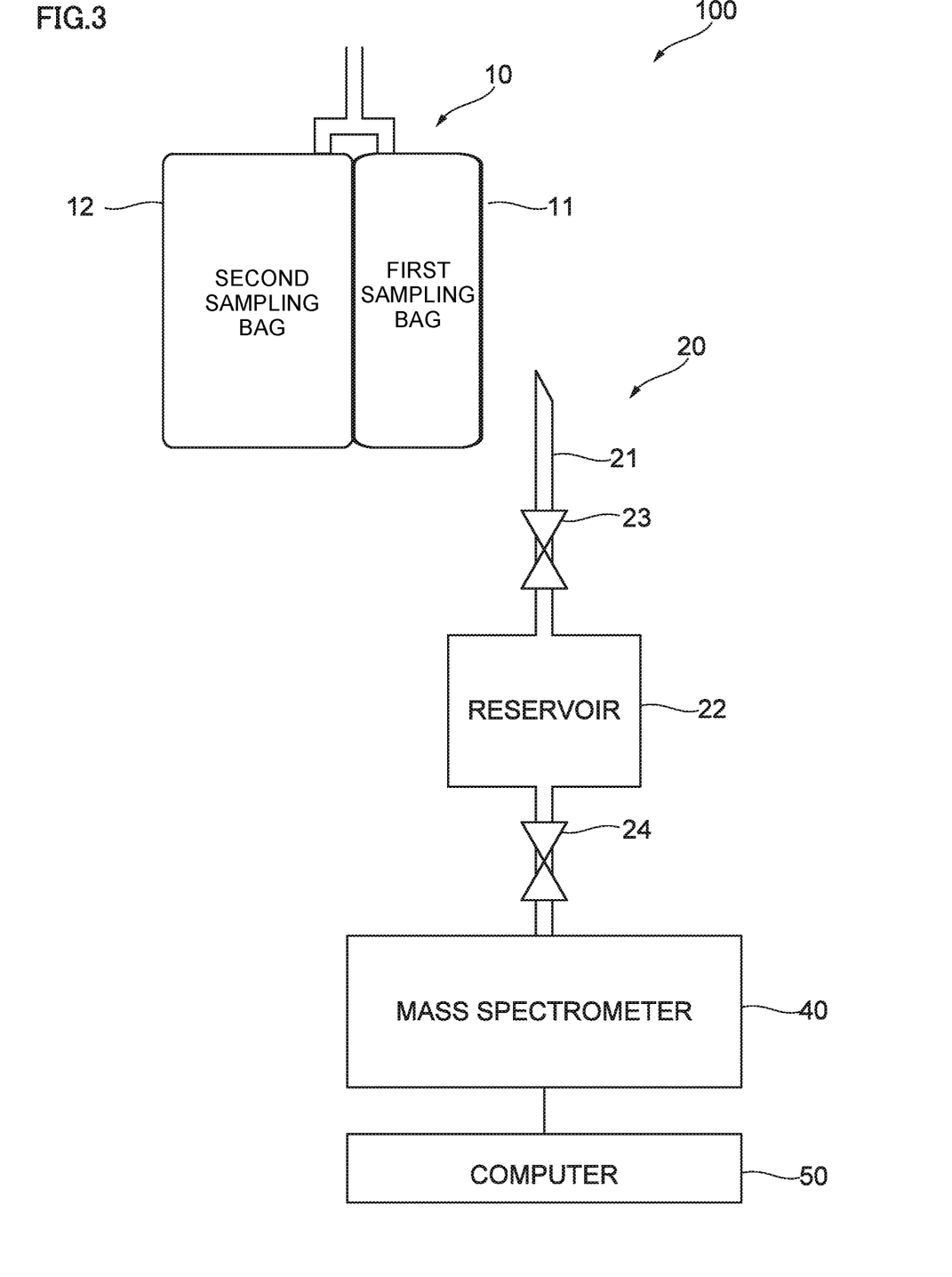
FIG. 3 depicts an example of a configuration of a breath gas measurement system according to a first exemplary embodiment.

Referring to FIG. 3, there is shown an example of a configuration of a breath gas measurement system 100 according to the first exemplary embodiment. As shown in FIG. 3, the breath gas measurement system 100 can include a sampling bag module 10, an inlet structure 20, a mass spectrometer 40, and a computer 50.

The sampling bag module 10 can include the first sampling bag 11 for storing the first breath sample, and the second sampling bag 12 for storing the second breath sample, as shown in FIG. 2. The sampling bag module 10 serves as one example of the claimed bag unit.

The inlet structure 20 can transfer the first breath sample and the second breath sample from the bag module 10 into the mass spectrometer 40. The inlet structure 20 serves as one example of the claimed transfer device. The inlet structure 20 can be connectable to the sampling bag module 10, and connected to the mass spectrometer 40. The inlet structure 20 can include a needle 21, a reservoir 22, an upper valve 23, and a lower valve 24.

The needle 21 can be manipulated to puncture the first sampling bag 11 to suck the first breath sample, and to puncture the second sampling bag 12 to suck the second breath sample, one by one. The needle 21 can have a length of 3 to 5 centimeters. The needle 21 can have a narrow inner diameter to minimize volume of environmental gas contamination. For example, the inner diameter can be greater than 30 gauges, e.g., smaller than 200 micrometers. Alternatively, the needle 21 can be automatically operated to puncture the first sampling bag 11 and the second sampling bag 12.

The reservoir 22 can store the first breath sample sucked into the needle 21 and store the second breath sample sucked into the needle 21, one by one. The reservoir 22 can have a predetermined volume much smaller than each of the volumes of the first sampling bag 11 and the second sampling bag 12. The predetermined volume can be, for example, 0.2 milliliters.

The upper valve 23 can be a valve provided on the upstream side of the reservoir 22 in the gas flow direction. The upper valve 23 can be manipulated to transfer the first breath sample from the first sampling bag 11 into the reservoir 22 when the first sampling bag 11 is punctured with the needle 21, and to transfer the second breath sample from the second sampling bag 12 into the reservoir 22 when the second sampling bag 12 is punctured with the needle 21. Alternatively, the upper valve 23 can be automatically operated to transfer the first breath sample and the second breath sample from the first sampling bag 11 and the second sampling bag 12, respectively, into the reservoir 22.

The lower valve 24 can be a valve provided on the downstream side of the reservoir 22 in the gas flow direction. The lower valve 24 can be manipulated to transfer the first breath sample from the reservoir 22 into the mass spectrometer 40, and to transfer the second breath sample from the reservoir 22 into the mass spectrometer 40. Alternatively, the lower valve 24 can be automatically operated to transfer the first breath sample and the second breath sample from the reservoir 22 into the mass spectrometer 40.

The mass spectrometer 40 can obtain the first mass spectral data by mass spectroscopy of the first breath sample, and obtain the second mass spectral data by mass spectroscopy of the second breath sample. The first mass spectral data and the second mass spectral data can be normalized based on mass spectral data of argon. This means that the ratio of raw data of the first mass spectral data to the mass spectral data of argon is taken as the final data of the first mass spectral data, and the ratio of raw data of the second mass spectral data to the mass spectral data of argon is taken as the final data of the second mass spectral data.

The computer 50 can subtract the first mass spectral data of the first breath sample obtained by the mass spectrometer 40 from the second mass spectral data of the second breath sample obtained by the mass spectrometer 40. The computer 50 serves as one example of the claimed data processor.

Figure 4:
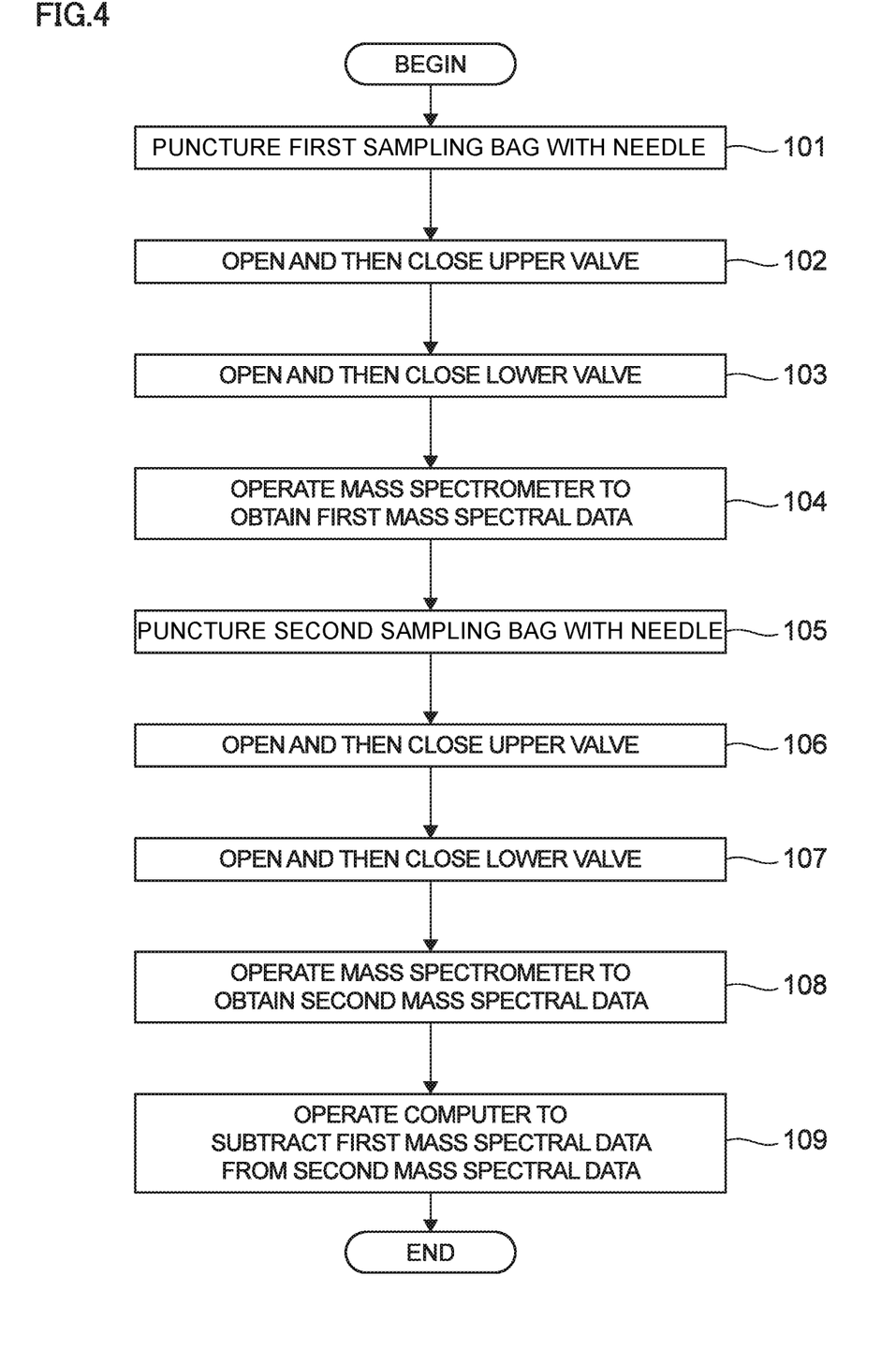
FIG. 4 depicts a flowchart representing an example of an operation of an operator who operates the breath gas measurement system according to the first exemplary embodiment.

Referring to FIG. 4, there is shown a flowchart representing an example of an operation of an operator who operates the breath gas measurement system 100 according to the first exemplary embodiment. Prior to the operation, the reservoir 22 is assumed to be kept at high vacuum by opening the lower valve 24 with the upper valve 23 closed.

First, the operator can puncture the first sampling bag 11 with the needle 21 (block 101). This can cause the first breath sample in the first sampling bag 11 to flow into the needle 21.

Next, the operator can open and then close the upper valve 23 (block 102). This can cause the first breath sample flowed into the needle 21 at block 101 to flow into the reservoir 22.

Next, the operator can open and then close the lower valve 24 (block 103). This can cause the first breath sample flowed into the reservoir 22 at block 102 to flow into the mass spectrometer 40.

In this state, the operator can operate the mass spectrometer 40 to obtain the first mass spectral data (block 104). According to this operation, the mass spectrometer 40 can obtain the first mass spectral data by mass spectroscopy of the first breath sample flowed into the mass spectrometer 40 at block 103.

On the other hand, the operator can puncture the second sampling bag 12 with the needle 21 (block 105). This can cause the second breath sample in the second sampling bag 12 to flow into the needle 21.

Next, the operator can open and then close the upper valve 23 (block 106). This can cause the second breath sample flowed into the needle 21 at block 105 to flow into the reservoir 22.

Next, the operator can open and then close the lower valve 24 (block 107). This can cause the second breath sample flowed into the reservoir 22 at block 106 to flow into the mass spectrometer 40.

In this state, the operator can operate the mass spectrometer 40 to obtain the second mass spectral data (block 108). According to this operation, the mass spectrometer 40 can obtain the second mass spectral data by mass spectroscopy of the second breath sample flowed into the mass spectrometer 40 at block 107.

After that, the operator can operate the computer 50 to subtract the first mass spectral data from the second mass spectral data (block 109). According to this operation, the computer 50 can subtract the first mass spectral data obtained at block 104 from the second mass spectral data obtained at block 108.

Note that, although blocks 101 to 104 are performed prior to blocks 105 to 108 in the above, blocks 105 to 108 can be performed prior to blocks 101 to 104.

Further, the operator is assumed to perform blocks 101 to 109 in the above, but the operator does not necessarily perform all of the blocks 101 to 109. A mechanism for controlling a relative position of the first sampling bag 11 to the needle 21 and a relative position of the second sampling bag 12 to the needle 21 can perform blocks 101 and 105. A mechanism for controlling the upper valve 23 can perform blocks 102 and 106, and a mechanism for controlling the lower valve 24 can perform blocks 103 and 107. Blocks 104 and 108 can be blocks for the mass spectrometer 40 to obtain the first mass spectral data and the second mass spectral data, respectively. Block 109 can be a block for the computer 50 to subtract the first mass spectral data from the second mass spectral data.

Figure 5:
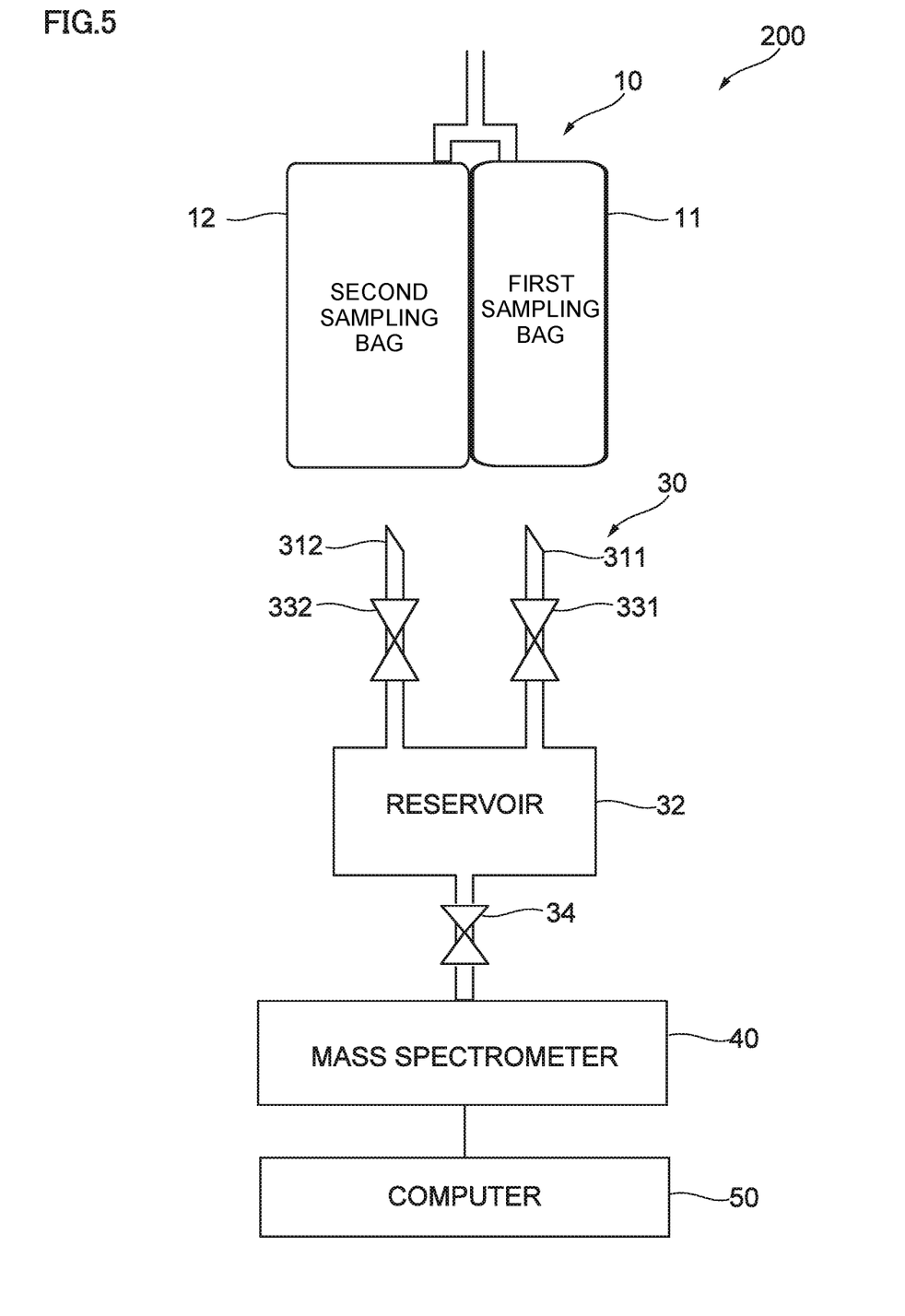
FIG. 5 depicts an example of a configuration of a breath gas measurement system according to a second exemplary embodiment.

Referring to FIG. 5, there is shown an example of a configuration of a breath gas measurement system 200 according to the second exemplary embodiment. As shown in FIG. 5, the breath gas measurement system 200 can include a sampling bag module 10, an inlet structure 30, a mass spectrometer 40, and a computer 50.

The sampling bag module 10 can include the first sampling bag 11 for storing the first breath sample, and the second sampling bag 12 for storing the second breath sample, as shown in FIG. 2. The sampling bag module 10 serves as one example of the claimed bag unit.

The inlet structure 30 can transfer the first breath sample and the second breath sample from the bag module 10 into the mass spectrometer 40. The inlet structure 30 serves as one example of the claimed transfer device. The inlet structure 30 can be connectable to the sampling bag module 10, and connected to the mass spectrometer 40. The inlet structure 30 can include a first needle 311, a second needle 312, a reservoir 32, a first upper valve 331, a second upper valve 332, and a lower valve 34.

The first needle 311 can be manipulated to puncture the first sampling bag 11 to suck the first breath sample. The second needle 312 can be manipulated to puncture the second sampling bag 12 to suck the second breath sample. Each of the first needle 311 and the second needle 312 can have a length of 3 to 5 centimeters. Each of the first needle 311 and the second needle 312 can have a narrow inner diameter to minimize volume of environmental gas contamination. For example, the inner diameter can be greater than 30 gauges, e.g., smaller than 200 micrometers. Alternatively, the first needle 311 and the second needle 312 can be automatically operated to puncture the first sampling bag 11 and the second sampling bag 12, respectively.

The reservoir 32 can store the first breath sample sucked into the first needle 311 and store the second breath sample sucked into the second needle 312, one by one. The reservoir 32 can have a predetermined volume much smaller than each of the volumes of the first sampling bag 11 and the second sampling bag 12. The predetermined volume can be, for example, 0.2 milliliters.

The first upper valve 331 and the second upper valve 332 can be valves provided on the upstream side of the reservoir 32 in the gas flow direction. The first upper valve 331 can be manipulated to transfer the first breath sample from the first sampling bag 11 into the reservoir 32. The second upper valve 332 can be manipulated to transfer the second breath sample from the second sampling bag 12 into the reservoir 32. Alternatively, the first upper valve 331 and the second upper valve 332 can be automatically operated to transfer the first breath sample and the second breath sample from the first sampling bag 11 and the second sampling bag 12, respectively, into the reservoir 32.

The lower valve 34 can be a valve provided on the downstream side of the reservoir 32 in the gas flow direction. The lower valve 34 can be manipulated to transfer the first breath sample from the reservoir 32 into the mass spectrometer 40, and to transfer the second breath sample from the reservoir 32 into the mass spectrometer 40. Alternatively, the lower valve 34 can be automatically operated to transfer the first breath sample and the second breath sample from the reservoir 32 into the mass spectrometer 40.

The mass spectrometer 40 can obtain the first mass spectral data by mass spectroscopy of the first breath sample, and obtain the second mass spectral data by mass spectroscopy of the second breath sample. The first mass spectral data and the second mass spectral data can be normalized based on mass spectral data of argon. This means that the ratio of raw data of the first mass spectral data to the mass spectral data of argon is taken as the final data of the first mass spectral data, and the ratio of raw data of the second mass spectral data to the mass spectral data of argon is taken as the final data of the second mass spectral data.

The computer 50 can subtract the first mass spectral data of the first breath sample obtained by the mass spectrometer 40 from the second mass spectral data of the second breath sample obtained by the mass spectrometer 40. The computer 50 serves as one example of the claimed data processor.

Figure 6:
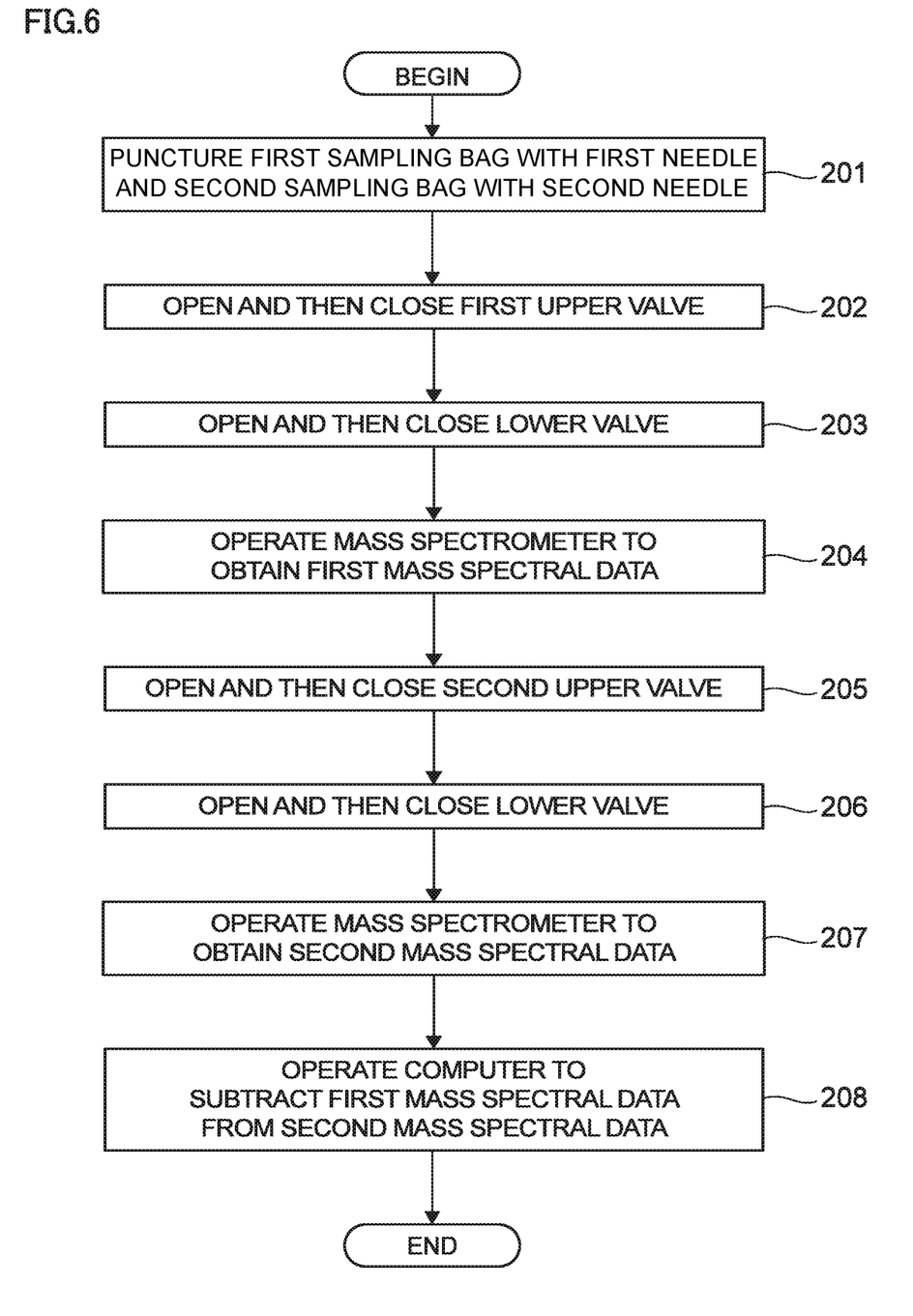
FIG. 6 depicts a flowchart representing an example of an operation of an operator who operates the breath gas measurement system according to the second exemplary embodiment.

Referring to FIG. 6, there is shown a flowchart representing an example of an operation of an operator who operates the breath gas measurement system 200 according to the second exemplary embodiment. Prior to the operation, the reservoir 32 is assumed to be kept at high vacuum by opening the lower valve 34 with the first upper valve 331 and the second upper valve 332 closed.

First, the operator can puncture the first sampling bag 11 with the first needle 311 and the second sampling bag 12 with the second needle 312 (block 201). This can cause the first breath sample in the first sampling bag 11 to flow into the first needle 311, and the second breath sample in the second sampling bag 12 to flow into the second needle 312.

Next, the operator can open and then close the first upper valve 331 (block 202). This can cause the first breath sample flowed into the first needle 311 at block 201 to flow into the reservoir 32.

Next, the operator can open and then close the lower valve 34 (block 203). This can cause the first breath sample flowed into the reservoir 32 at block 202 to flow into the mass spectrometer 40.

In this state, the operator can operate the mass spectrometer 40 to obtain the first mass spectral data (block 204). According to this operation, the mass spectrometer 40 can obtain the first mass spectral data by mass spectroscopy of the first breath sample flowed into the mass spectrometer 40 at block 203.

On the other hand, the operator can open and then close the second upper valve 332 (block 205). This can cause the second breath sample flowed into the second needle 312 at block 201 to flow into the reservoir 32.

Next, the operator can open and then close the lower valve 34 (block 206). This can cause the second breath sample flowed into the reservoir 32 at block 205 to flow into the mass spectrometer 40.

In this state, the operator can operate the mass spectrometer 40 to obtain the second mass spectral data (block 207). According to this operation, the mass spectrometer 40 can obtain the second mass spectral data by mass spectroscopy of the second breath sample flowed into the mass spectrometer 40 at block 206.

After that, the operator can operate the computer 50 to subtract the first mass spectral data from the second mass spectral data (block 208). According to this operation, the computer 50 can subtract the first mass spectral data obtained at block 204 from the second mass spectral data obtained at block 207.

Note that, although blocks 202 to 204 are performed prior to blocks 205 to 207 in the above, blocks 205 to 207 can be performed prior to blocks 202 to 204.

Further, the operator is assumed to perform blocks 201 to 208 in the above, but the operator does not necessarily perform all of the blocks 201 to 208. A mechanism for controlling a relative position of the first sampling bag 11 to the first needle 311 and a relative position of the second sampling bag 12 to the second needle 312 can perform block 201. A mechanism for controlling the first upper valve 331 and a mechanism for controlling the second upper valve 332 can perform blocks 202 and 205, respectively, and a mechanism for controlling the lower valve 34 can perform blocks 203 and 206. Blocks 204 and 207 can be blocks for the mass spectrometer 40 to obtain the first mass spectral data and the second mass spectral data, respectively. Block 208 can be a block for the computer 50 to subtract the first mass spectral data from the second mass spectral data.

What is claimed is:

1. A method for sampling breath gas, the method comprising:
    collecting a first breath sample in a first bag, the first breath sample being an initial part of expired gas expired after inspiration;
    collecting a second breath sample in a second bag, the second breath sample being a latter part of the expired gas; and
    subtracting first mass spectral data from second mass spectral data, the first mass spectral data being obtained by mass spectroscopy of the first breath sample collected in the first bag, the second mass spectral data being obtained by mass spectroscopy of the second breath sample collected in the second bag.

2. The method of claim 1, wherein the first breath sample is a predetermined volume of the expired gas expired immediately after the inspiration.

3. The method of claim 2, wherein the second breath sample is another predetermined volume of the expired gas expired at a predetermined interval after expiration of the first breath sample.

4. The method of claim 1, wherein the first breath sample includes gas which has come out of anatomical dead space without reaching lungs.

5. The method of claim 4, wherein the second breath sample includes gas which has come out of the lungs after reaching the lungs.

6. The method of claim 1, wherein the first mass spectral data and the second mass spectral data are normalized based on mass spectral data of argon.

7. An apparatus for sampling breath gas, the apparatus comprising:
- a first bag;
- a second bag; and
- a controller for controlling a first breath sample to flow in the first bag and controlling a second breath sample to flow in the second bag so that first mass spectral data is subtracted from second mass spectral data, the first breath sample being an initial part of expired gas expired after inspiration, the second breath sample being a latter part of the expired gas, the first mass spectral data being obtained by mass spectroscopy of the first breath sample in the first bag, the second mass spectral data being obtained by mass spectroscopy of the second breath sample in the second bag.

8. The apparatus of claim 7, wherein the first breath sample is a predetermined volume of the expired gas expired immediately after the inspiration.

9. The apparatus of claim 8, wherein the second breath sample is another predetermined volume of the expired gas expired at a predetermined interval after expiration of the first breath sample.

10. The apparatus of claim 7, wherein the first breath sample includes gas which has come out of anatomical dead space without reaching lungs.

11. The apparatus of claim 10, wherein the second breath sample includes gas which has come out of the lungs after reaching the lungs.

12. The apparatus of claim 7, wherein the first mass spectral data and the second mass spectral data are normalized based on mass spectral data of argon.

13. A system for analyzing breath gas, the system comprising:
- a bag unit which includes a first bag and a second bag, the first bag being a bag in which a first breath sample is collected, the first breath sample being an initial part of expired gas expired after inspiration, the second bag being a bag in which a second breath sample is collected, the second breath sample being a latter part of the expired gas;
- a mass spectrometer which obtains first mass spectral data and second mass spectral data, the first mass spectral data being obtained by mass spectroscopy of the first breath sample collected in the first bag, the second mass spectral data being obtained by mass spectroscopy of the second breath sample collected in the second bag; and
- a data processor which subtracts the first mass spectral data from the second mass spectral data.

14. The system of claim 13, wherein the first breath sample is a predetermined volume of the expired gas expired immediately after the inspiration.

15. The system of claim 14, wherein the second breath sample is another predetermined volume of the expired gas expired at a predetermined interval after expiration of the first breath sample.

16. The system of claim 13, wherein the first breath sample includes gas which has come out of anatomical dead space without reaching lungs.

17. The system of claim 16, wherein the second breath sample includes gas which has come out of the lungs after reaching the lungs.

18. The system of claim 13, wherein the first mass spectral data and the second mass spectral data are normalized based on mass spectral data of argon.

19. The system of claim 13, further comprising a transfer device for transferring the first breath sample and the second breath sample from the bag unit into the mass spectrometer, the transfer device comprising:
- a needle;
- a reservoir connected to the mass spectrometer;
- an upper valve provided between the needle and the reservoir; and
- a lower valve provided between the reservoir and the mass spectrometer, wherein
the transfer device performs a method comprising:
- puncturing the first bag with the needle;
- opening and then closing the upper valve to transfer the first breath sample from the first bag into the reservoir;
- opening and then closing the lower valve to transfer the first breath sample from the reservoir into the mass spectrometer;
- puncturing the second bag with the needle;
- opening and then closing the upper valve to transfer the second breath sample from the second bag into the reservoir;
- opening and then closing the lower valve to transfer the second breath sample from the reservoir into the mass spectrometer.

20. The system of claim 13, further comprising a transfer device for transferring the first breath sample and the second breath sample from the bag unit into the mass spectrometer, the transfer device comprising:
- a first needle;
- a second needle;
- a reservoir connected to the mass spectrometer;
- a first upper valve provided between the first needle and the reservoir;
- a second upper valve provided between the second needle and the reservoir; and
- a lower valve provided between the reservoir and the mass spectrometer, wherein
the transfer device performs a method comprising:
- puncturing the first bag with the first needle and the second bag with the second needle;
- opening and then closing the first upper valve to transfer the first breath sample from the first bag into the reservoir;
- opening and then closing the lower valve to transfer the first breath sample from the reservoir into the mass spectrometer;
- opening and then closing the second upper valve to transfer the second breath sample from the second bag into the reservoir;
- opening and then closing the lower valve to transfer the second breath sample from the reservoir into the mass spectrometer.

* * * * *